United States Patent
Moulinier

(10) Patent No.: US 11,918,371 B2
(45) Date of Patent: Mar. 5, 2024

(54) METHOD OF DETERMINING A SKIN OR HAIR BEAUTY RITUAL ASSOCIATED WITH A SPECIFIC USER

(71) Applicant: IEVA, Paris (FR)

(72) Inventor: David Moulinier, Lyons (FR)

(73) Assignee: IEVA, Paris (FR)

( * ) Notice: Subject to any disclaimer, the term of this patent is extended or adjusted under 35 U.S.C. 154(b) by 385 days.

(21) Appl. No.: 17/249,982

(22) Filed: Mar. 19, 2021

(65) Prior Publication Data

US 2021/0290150 A1 Sep. 23, 2021

(30) Foreign Application Priority Data

Mar. 23, 2020 (FR) .................................. 2002786

(51) Int. Cl.
| | |
|---|---|
| *G06K 9/00* | (2022.01) |
| *A61B 5/00* | (2006.01) |
| *A61B 5/103* | (2006.01) |
| *G06T 7/00* | (2017.01) |
| *G16H 10/20* | (2018.01) |

(Continued)

(52) U.S. Cl.
CPC .......... *A61B 5/4272* (2013.01); *A61B 5/1034* (2013.01); *A61B 5/441* (2013.01); *A61B 5/7264* (2013.01); *G06T 7/0012* (2013.01); *G16H 10/20* (2018.01); *G16H 20/10* (2018.01); *G16H 50/20* (2018.01); *A45D 2044/007* (2013.01); *A61B 2560/0242* (2013.01); *G06T 2207/20084* (2013.01)

(58) Field of Classification Search
None
See application file for complete search history.

(56) References Cited

U.S. PATENT DOCUMENTS

| | | |
|---|---|---|
| 2003/0065636 A1 | 4/2003 | Peyrelevade |
| 2006/0020183 A1 | 1/2006 | Pershing |
| 2019/0369119 A1* | 12/2019 | Zhuang .............. G01N 33/6881 |

FOREIGN PATENT DOCUMENTS

| | | |
|---|---|---|
| EP | 3522772 | 8/2019 |
| FR | 2954837 | 7/2011 |

(Continued)

OTHER PUBLICATIONS

Search Report issued in FR application No. 2002786, dated Jan. 18, 2021.

*Primary Examiner* — Wei Wen Yang
(74) *Attorney, Agent, or Firm* — Knobbe Martens Olson & Bear LLP

(57) ABSTRACT

A method is for determining a beauty ritual. The method includes performing a beauty diagnosis of a user, and determining a generic beauty ritual including a set of recommended products selected according to the beauty diagnosis. Each recommended product is associated with a generic dosage and a generic prescription for use. The method further includes measuring, over time, the external stress undergone by the user with an environment sensor carried by the user during a period of time. At each increment of the period, the generic dosage and/or the generic prescription for use of the generic beauty ritual is modified based on the measured external stress to obtain a beauty ritual with recommended products having a dosage and/or a prescription for use enabling to respond to the external stress undergone by the user.

14 Claims, 5 Drawing Sheets

(51) Int. Cl.
*G16H 20/10* (2018.01)
*G16H 50/20* (2018.01)
*A45D 44/00* (2006.01)

(56) References Cited

FOREIGN PATENT DOCUMENTS

| WO | WO 2017/095854 | 8/2017 | | |
|---|---|---|---|---|
| WO | WO 2017/165363 | 9/2017 | | |
| WO | WO 2018/065380 | 4/2018 | | |
| WO | WO-2018065380 A1 * | 4/2018 | ........... | A61B 5/0071 |
| WO | WO 2018/222808 | 12/2018 | | |
| WO | WO-2019148116 A1 * | 8/2019 | ............. | A45D 44/00 |

* cited by examiner

METHOD OF DETERMINING A SKIN OR HAIR BEAUTY RITUAL ASSOCIATED WITH A SPECIFIC USER

TECHNICAL BACKGROUND

The invention concerns a method of determining a beauty ritual associated with a specific user. The invention may apply to the determination of both a skin or a hair ritual.

The invention particularly advantageously applies in the field of cosmetics, where it is desired to be able to provide a cream tailored for the needs for treatment of a user's skin.

The invention more particularly aims at improving the relevance of the propositions of the ritual by taking into account the lifestyle and each user's environment.

STATE OF THE ART

Cosmetic products have evolved in the last years to specifically respond to the beauty needs of a user's skin. For this purpose, a plurality of solutions now provide testing the physiological characteristics of a user's skin to guide her/him towards the purchase of a product adapted to her/his needs.

Instead of recommending the purchase of a standard product, company IOMA provides a solution called "IOMA In.Lab" This solution uses devices such as "IOMA Sphere", "IOMA Mirror", or "IOMA Link", present in outlets, to formulate a tailor-made product according to the results of the measurements of the physiological characteristics of a user's skin by these devices. However, the content of this product is devised for an uninterrupted use over a minimum period of one month.

Now, the physiological parameters of a user's skin may vary over time and it is desired to be able to formulate tailor-made treatments which vary daily according to the stress undergone by the user's skin.

For this purpose, document EP 3 522 772 of the Applicant provides determining the physiological properties of a specific user's skin by means of a contact sensor and of an environment sensor. The contact sensor enables to regularly perform, typically in the morning and in the evening, a local measurement of certain physiological properties. In addition to the contact sensor, the environment sensor is carried all day long by the user to evaluate the external stress undergone by the skin during the day and enable to qualify the measurements obtained by the contact sensor.

With these specific measurements of the physiological parameters, it is possible to recommend a beauty ritual adapted to each user and capable of varying over time. The user thus obtains a ritual that may be different from one day to the other, according to the variation of her/his physiological parameters.

Certain solutions enable to manufacture the product at home due to the use of single-use capsules. For this purpose, several companies provide machines for formulating a tailor-made cosmetic product, for example, Romy®'s "HyLab" formulator or L'Oréal®'s "Custom D.O.S.E" solution having its machine described in patent WO 2017/95854. However, these solutions provide a formulation based on little reliable parameters originating from a photograph of a face by a smartphone, with no verification of the measurement conditions.

In the case of these machines, the user has a number of single-use capsules containing the compounds of the different products that she/he can formulate from the machine. During the product manufacturing, the machine extracts the desired quantities of the compounds present in the different inserted capsules. The machine then mixes the extracted compounds to obtain a product having an appearance corresponding to a standard product but having its compounds and their quantities determined to measure.

However, there is an issue linked to the management of the products provided to perform the beauty ritual. Indeed, environmental parameters vary constantly, which causes a modification of the beauty ritual via the proposition of new products or of a new formulation of products.

Now, certain products, responding to a very specific environmental stimulation, are only very occasionally provided in the ritual. Thus, for a specific user, this model tends towards the overconsumption and the waste of products, causing cost issues for the user and pollution issues for the environment.

For example, for Romy®'s "HyLab" formulator or L'Oréal®'s "Custom D.O.S.E" solution, the products proposed by the ritual may be impossible to manufacture, for example, when the user does not have the recommended single-use capsules. This system thus encourages the user to consume a new product.

Further, recent studies tend to demonstrate that the efficiency of a product is not only linked to these physiological parameters, but also to the user's lifestyle.

Accordingly, the technical problem that the present invention aims at solving thus is to determine a beauty ritual associated with a specific user, limiting product purchase costs for the user as well as the environmental footprint and taking into account the user's lifestyle and environment to offer an anticipative ritual enabling to act before the skin's physiological parameters are modified.

SUMMARY

To respond to this technical problem, the invention provides determining a generic ritual according to a user's initial physiological parameters and recursively varying this ritual to adapt this ritual via the analysis of the user's lifestyle and environment.

For this purpose, the dosage and/or the prescription of the different products of the generic ritual are adjusted at each iteration according to the measurements acquired over time. By iteratively adjusting the dosages and/or the prescription instead of searching every day for a new ritual, the user thus obtains a more complete and more optimized use of the provided products, limiting its consumption and its environmental footprint.

For this purpose, the invention concerns a method of determining a skin or hair beauty ritual, associated with a specific user, said method comprising the steps of:
  performing at least one beauty diagnosis of said user;
  determining a generic beauty ritual comprising a set of recommended products, said recommended products being selected according to said beauty diagnosis; each recommended product being associated with a generic dosage and a generic prescription for use;
  measuring, over time, the external stress undergone by said user by means of at least one environment sensor carried by said user during a period; and
  at each increment of said period, modifying said generic dosage and/or said generic prescription for use of said generic beauty ritual according to the external stress measured since the beginning of said period, to obtain, at each increment of said period, a beauty ritual with recommended product having a dosage and/or a prescription for use enabling to respond to the external stress undergone through said user's lifestyle.

The invention thus enables to obtain a beauty ritual recursively varying according to the external stress undergone by the user. This feedback loop, placed on the generic ritual and obtained from the health diagnosis, enables to give a preponderating place to the user's lifestyle and environment.

The beauty diagnosis may comprise steps from among the following list, these steps may be taken separately or in combination.

According to an embodiment, the beauty diagnosis comprises a questionnaire configured to determine the user's needs and beauty habits. Thus, it is possible to know the user's habits and to adapt the generic beauty ritual according to these habits. For example, if a user is not used to perform a beauty ritual in the morning and/or in the evening, the generic beauty ritual will comprise a more minimalistic prescription than for a user used to more regularly use products.

According to an embodiment, the beauty diagnosis comprises a step of estimation of the age of said user's skin, carrying out the steps of:
  taking a picture of said user's face;
  detecting a matrix of characteristic points on said picture; and
  determining an age of said user's skin by means of a neural network configured to analyze the position of said characteristic points and comparing these positions with the positions of characteristic points of reference faces for which the person's age is known.

In the sense of the invention, the terms "characteristic points" refer to a property extracted from the image and used as a classification key.

In other words, the neural network uses pictures of faces of person having a known age to assign an apparent age to the user's skin. Thereby, the beauty ritual may be adapted to recommend products adapted to the apparent age of the user's skin.

According to an embodiment, the beauty diagnosis comprises a step of estimation of said user's phototype, carrying out the sub-steps of:
  taking a picture including said user's face and a colorimetric patch comprising a reference color scale;
  comparing an average color of said user's face with the different reference colors present on said colorimetric patch; and
  determining a phototype of said user according to a maximum similarity between said average color and a color among the different reference colors present on said colorimetric patch.

This embodiment enables to determine the color contained in the color scale which is closest to the average color of the user's skin. Preferably, said step of estimation of the phototype uses a colorimetric patch comprising the 6 colors of Fitzpatrick's classification.

The phototype corresponds to the characteristics of reaction to sun of the user's skin.

Thus, the determination of the phototype enables to define a sun protection index necessary for the user's skin type. For example, a person having a low phototype will be much more sensitive to cold than a person having a high phototype. Further, her/his skin will be much more reactive to a cold wind, for example. The products of the ritual thus take into account this "over-reactivity" of the skin. Further, a person with a very low phototype will be very sun-sensitive and will require a sun protection having an index greater than or equal to 50 SPF while a person having a darker skin color will be less sun-sensitive and will require a lower sun protection index, which lets the skin synthesize vitamin D, necessary to the proper functioning of the body.

According to an embodiment, the health diagnosis comprises a step of estimation of a sebum rate of a specific area of said user's face, carrying out the sub-steps of:
  applying a sebum patch to said specific area; said patch having a reference surface and a measurement surface covered with an absorbing surface; said measurement surface and said absorbing surface having two distinct colors; said reference surface having a reference color;
  removing said sebum patch, after a predetermined time period, so that said absorbing surface becomes at least partially transparent by absorbing the sebum present on said specific area; said measurement surface becoming at least partially visible;
  taking a picture of said sebum patch in such a way as to include said reference surface and said measurement surface; and
  determining, on the picture, a sebum rate by analysis of a transparency percentage of said absorbing surface with respect to said reference color.

Preferably, said step of estimation of a sebum rate is carried out several times on a plurality of specific areas of said user's face. For example, the sebum rate may be measured on the forehead, the nose, the chin, and the cheeks.

Sebum resulting in acne and/or a bad appearance of the complexion, its regulation is one of the user's main objectives. The use of a sebum patch to determine the sebum rate of different face areas enables to adapt the beauty ritual by for example providing applying a different cream on areas having more or less sebum. Typically, a cream regulating the sebum on the T area (forehead, nose, chin) and a hydrating cream on the rest of the face.

According to an embodiment, the health diagnosis comprises a step of estimation of a scale rate of a specific area of said user's face, carrying out the sub-steps of:
  applying a peeling patch on said specific area; said patch having an adhesive measurement surface and a reference surface having two distinct colors;
  removing said peeling patch, after a predetermined time period, so that said adhesive measurement surface has a modified appearance due to the presence of dead cells;
  taking a picture of said peeling patch in such a way as to include said adhesive measurement surface and said reference surface; and
  determining, on the picture, a scale rate by analysis of a percentage of said adhesive surface modified by the presence of dead cells with respect to a color of said reference surface.

Preferably, said sub-step of determination of a scale rate is carried out via a neural network configured to compare the percentage of said adhesive surface modified by the presence of dead cells with reference images having a percentage of said modified adhesive surface corresponding to a determined scale rate.

In addition to the regulation of the sebum rate, a good hydration of the skin is the second factor most searched by the users. The use of a peeling patch enables to estimate this scale rate, that is, the number of dead cells present on the skin. A large number of dead cells is the sign of a skin dehydration. The peeling patch thus enables to adapt the quantity of hydrating cream or of water recommended by the beauty ritual.

Advantageously, said sebum patch and said peeling patch comprise an identification element; said picture being taken by incorporating said identification element so that said step of determining the scale rate and said step of determining the sebum rate can be carried out by identifying the nature of the patch.

This identification step enables the user to apply any of the sebum or peeling patches without previously having to indicate, to the application carrying out the determination step, which patch is used. Further, this identification step may also improve the traceability and the control of the quality of the patches if incoherent results linked to defective patches are detected.

According to an embodiment, the beauty diagnosis is established at regular intervals to modify the generic dosage and/or the generic prescription for use of the generic beauty ritual according to the new beauty diagnosis. This embodiment enables to form a second feedback loop to improve the relevance of the provided dosages and prescriptions.

Further, this embodiment also enables to account for the variation of the appearance of the user's skin or hair. Thus, this embodiment enables to prove the efficiency or the inefficiency of a ritual due to a concrete estimation of the variation of physiological parameters, such as the age of the skin or the hydration rate.

According to an embodiment, the environment sensor is integrated in a connected jewel or watch. For example, the environment sensor may correspond to the Applicant's "Twin-C" jewel. This "Twin-C" jewel particularly integrates temperature, pollution, and humidity sensors.

BRIEF DESCRIPTION OF THE DRAWINGS

The way to implement the present invention, as well as the resulting advantages, will better appear from the description of the following embodiments, in relation with the accompanying drawings, in which.

DESCRIPTION OF EMBODIMENTS

Figure 1A:
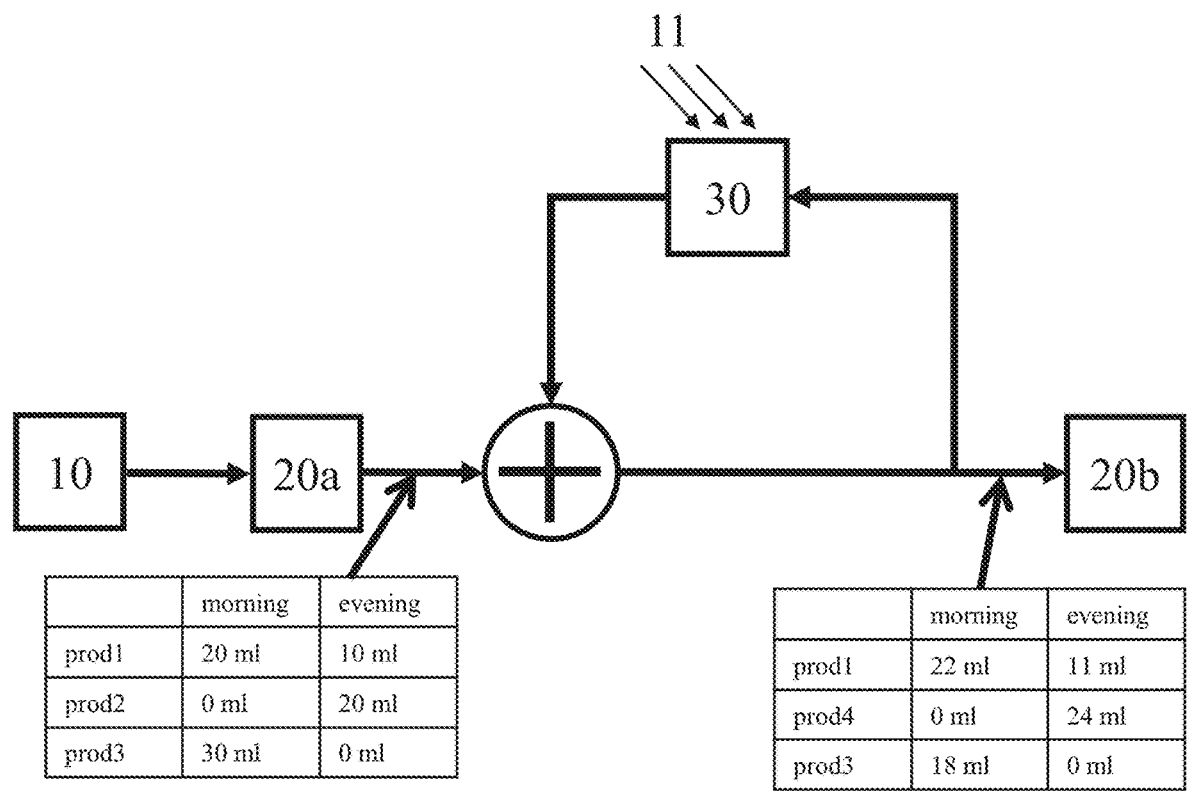
FIG. 1a is a simplified representation of the steps of a method of determining a beauty ritual according to a first embodiment of the invention.
Figure 1B:
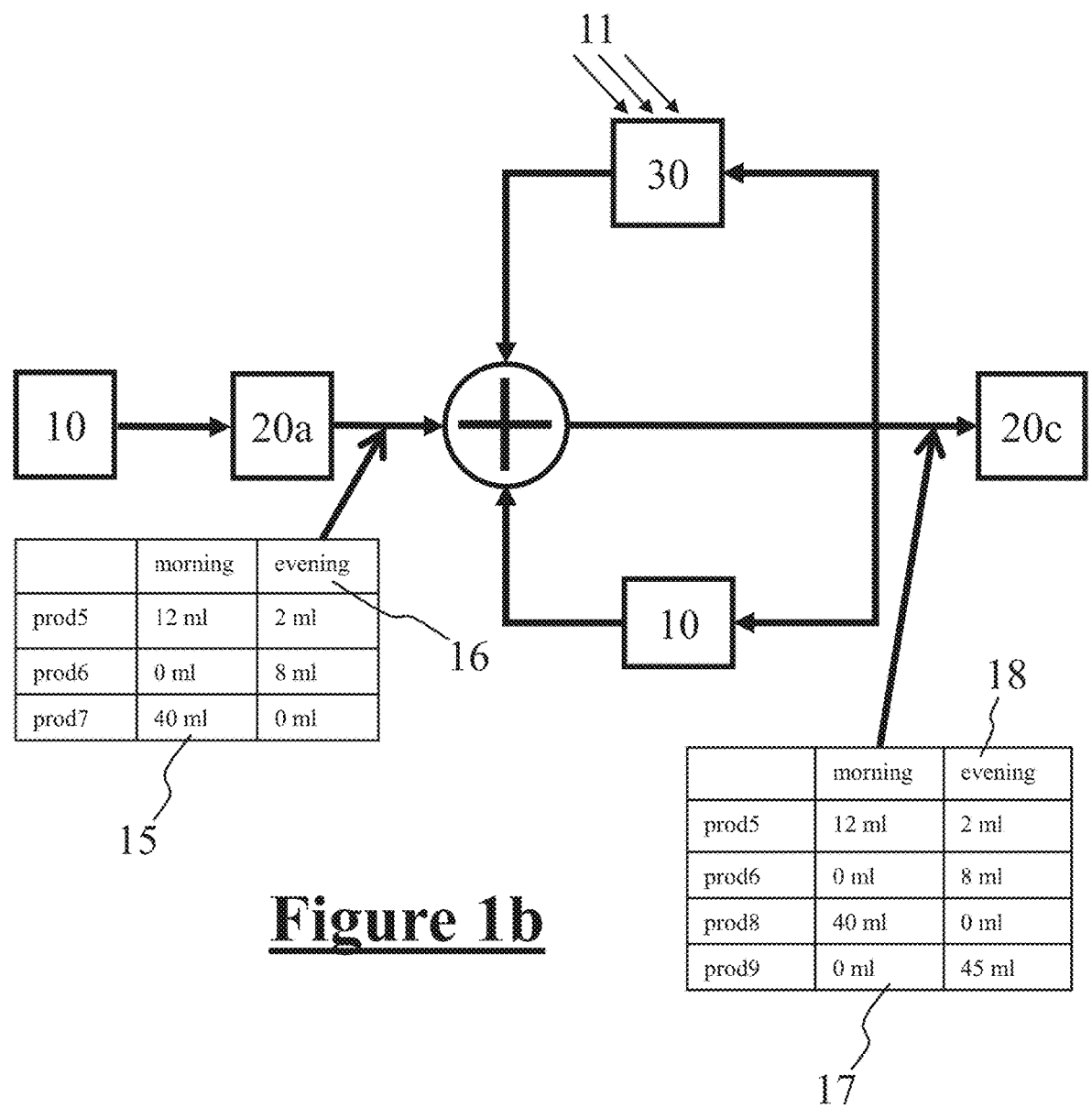
FIG. 1b is a simplified representation of the steps of a method of determining a beauty ritual according to a second embodiment of the invention.

As illustrated in FIGS. 1a and 1b, the method of determining a beauty ritual 20b comprises a plurality of preliminary steps 10-20a and at least one iterative step 30-10 repeated at regular intervals to adapt beauty ritual 20b-20c.

The following description describes the applications of the method of determining a beauty ritual 20b-20c to the face skin, however such a ritual may be applicable mutatis mutandis to other body areas such as the skin of the rest of the body or even the hair.

In a first step, a beauty diagnosis 10 is carried out. This diagnosis comprises a plurality of steps of analysis of physiological and psychological parameters of a user. It enables to determine a first generic beauty ritual 20a which roughly corresponds to the user's needs and objectives. This ritual is then refined over time via the analysis of results originating from an environment sensor 30.

Environment sensor 30 measures at regular intervals, or continuously, environmental parameters 11 such as the ambient noise, the temperature, the pollution rate, the quantity of UVs, the luminosity and/or humidity; which may have an impact on the appearance of the skin.

For example, sensor 30 may perform a measurement of the outdoor and indoor environment and estimate the quality of the air breathed outdoors but also inside of the life or work spaces of the use.

Environment sensor 30 may be embarked in a connected jewel, such as the Applicant's "Twin.C" jewel, a connected watch, or a smartphone.

The data recorded by environment sensor 30 are transmitted to the smartphone and accessible via an application. It then becomes possible to follow at any time the variation of the environmental parameters 11 and to estimate their possible impacts on the user's skin.

To prevent the negative impacts of the different environmental parameters 11 measured by sensor 30, the generic beauty ritual 20a is modified. The dosages 15 and the prescription 16 of certain products already present in the generic beauty ritual 20a may be modified and/or certain products may be suppressed and others may be added. For example, during a pollution wave, an anti-pollution treatment may be added to the generic beauty ritual 20a, to prevent a premature aging of the skin.

Similarly, beauty ritual 20b-20b may be modified by nutritional and behavioral recommendations. For example, beauty ritual 20b-20c may recommend drinking to avoid dehydration in case of a heat wave, eating more food containing beta-carotene to fight skin aging.

As illustrated in FIG. 1a, a single feedback loop is applied to the generic beauty ritual 20a by means of environment sensor 30. The generic beauty ritual 20a may prescribe the use of three products Prod1, Prod2, and Prod3. More particularly, the generic beauty ritual 20a may prescribe the use of 20 mL of product Prod1 in the morning and 10 mL of product Prod1 in the evening, 0 mL of product Prod2 in the morning and 20 mL of product Prod2 in the evening, as well as 30 mL of product Prod3 in the morning and 0 mL of product Prod3 in the evening.

Over time and along the measurements performed by environment sensor 30, beauty ritual 20b may vary to refine the dosage and/or the prescription of all these products. As illustrated in FIG. 1a, for a given time, beauty ritual 20b provides using product Prod1 with a dosage of 22 mL in the morning and of 11 mL in the evening and no longer provides using product Prod2. Instead, a product Prod4 is recommended with a use of 0 mL in the morning and 24 mL in the evening. The use of product Prod3 has also been greatly modified to recommend the use of 18 mL in the morning and of 0 mL in the evening.

In an embodiment described in FIG. 1b, beauty diagnosis 10 is regularly repeated, typically every month or every 6 months, to estimate, by means of concrete physiological parameters, the variation of the skin quality. Thus, this embodiment describes the use of two feedback loops enabling to obtain a beauty ritual 20c. With this embodiment, the user can measure the efficiency of beauty ritual 20c by comparing the actual quality of her/his skin with the previously-recorded data.

Similarly, the generic beauty ritual 20a of FIG. 1b provides the use of three products Prod5, Prod6, and Prod7.

More particularly, generic beauty ritual 20a provides using 12 mL of product Prod5 in the morning and 20 mL of product Prod5 in the evening as well as 0 mL of product Prod6 in the morning and 8 mL of product Prod6 in the evening, as well as 40 mL of product Prod7 in the morning and 0 mL of product Prod7 in the evening. At the end of two feedback loops, the regular use of beauty ritual 20b is targeted, the latter may be modified as illustrated in FIG. 1b to recommend the use of four products Prod5, Prod6, Prod8, and Prod9. More particularly, it may be recommended to use 12 mL of product Prod5 in the morning and 2 mL of product Prod5 in the evening, 0 mL of product Prod6 in the morning and 8 mL of product Prod6 in the evening, 40 mL of product Prod8 in the morning and 0 mL of product Prod8 in the evening, and 0 mL of product Prod9 in the morning and 45 mL of product Prod9 in the evening.

Of course, these values only illustrate an example of implementation and of variation of the recommended products between generic beauty ritual 20a and beauty ritual 20b-20c varying over time.

Figure 2:
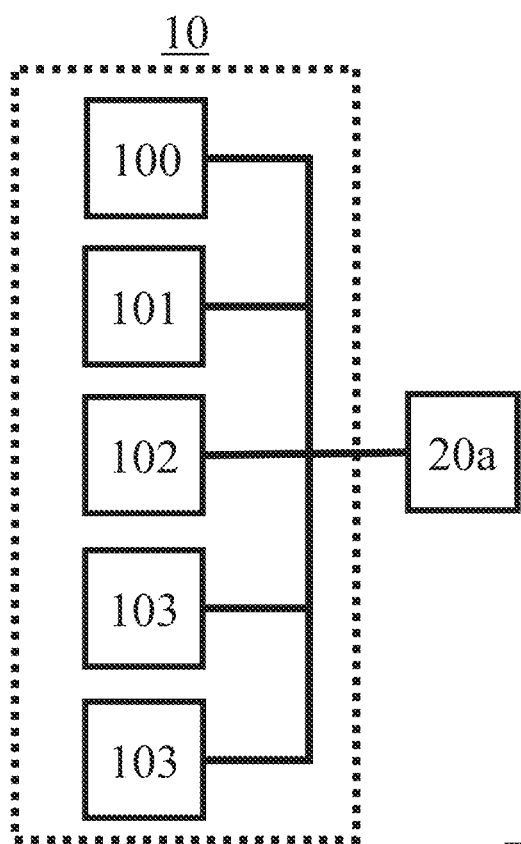
FIG. 2 is a simplified representation detailing an embodiment of the beauty diagnosis of the embodiments of FIGS. 1a and 1b.
Figure 3:
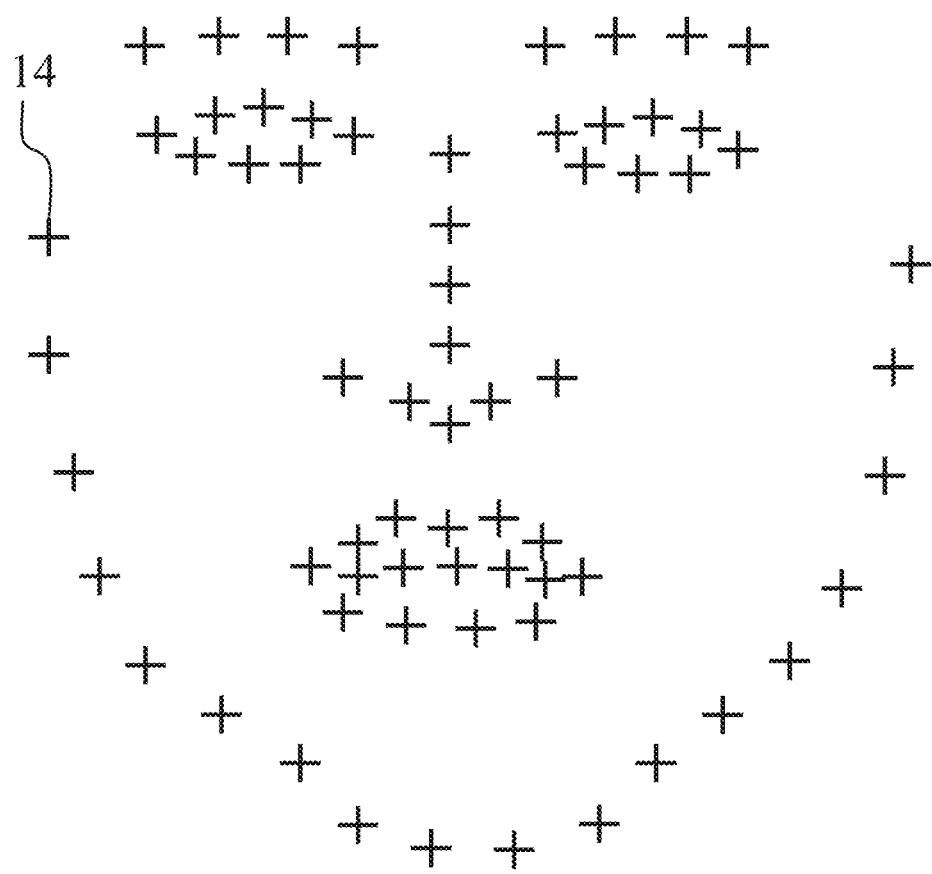
FIG. 3 is a representation of a matrix of characteristic points of a user's face.

As illustrated in FIG. 2, beauty diagnosis 10 measures a plurality of parameters. In a first questionnaire step 100, the user is invited, via the application, to fill in a questionnaire 100 on her/his habits, preferences, and knowledge of her/his skin and/or hair. For example, questionnaire 100 may ask the user about the type of skin that she/he believes having (oily, mixed, dehydrated), on her/his daily habits (quantity of water drunk in a day, number of products applied to the skin in the morning and/or in the evening . . . ), but also on her/his age, size, weight . . . .

Indeed, it is important to match the user's perception and personal objectives with the provided beauty ritual 20b-20c. A user who does not feel concerned by the recommendations of beauty ritual 20b-20c will tend to less respect these recommendations.

A second step of estimation of an apparent age 101 asks, for example, the user to take a picture of her/his face via her/his smartphone camera.

The picture is analyzed by a neural network configured to detect a matrix of characteristic points 14 on the picture; and determine an age of the user's skin by comparing the position of characteristic points 14 with the positions of characteristic points of reference faces for which the person's age is known.

More particularly, the neural network may have a convolutional architecture using the residual learning paradigm enabling to extract the matrix of characteristic points 14 of the user's face. It is then possible to determine, for example, the size and the spacing of the eyes, the size of the nose, of the mouth, the shape of the face . . . .

This matrix is supplied at the input of a model based on a succession of regression, segmentation algorithms, and of classifiers having been submitted to a training based on the reference faces having a known gender and age.

At the end of this image processing, an apparent skin age is delivered to the user.

In the case where the apparent age is greater than the user's real age, generic beauty ritual 20a is adapted to integrate anti-aging products intended to decrease the user's apparent age to have it match with her/his real age. In the inverse case, generic beauty ritual 20a will comprise products enabling to maintain the user's apparent skin age.

An analysis of the wrinkles, of the hydration, of the pore dilation, or also of the presence of sebum may also be performed on the picture of the apparent age estimation step 101. However, this analysis is highly dependent on the quality of the picture and may be preferably completed by the next steps.

A third step of estimation of phototype 102 asks the user to take a picture of her/his face and/or hair via her/his smartphone camera. However, the picture must also include a colorimetric patch showing a skin color scale. The advantage of taking a picture comprising both the face and the patch is to decrease the impact of the conditions in which the picture is taken. The patch may for example be placed against the user's cheek to allow a direct comparison.

The same neural network architecture using the residual learning paradigm is preferably used to extract a matrix of characteristic points of the user's face. A user's carnation, also called phototype, is then estimated by a comparative analysis of the average color of the user's skin with this color scale. For example, the LAB and HSV colorimetric spaces, which enable to separate the luminance and the saturation of the color, may be used.

The steps of estimation of an apparent age 101 and of the phototype 102 may be carried out separately by taking two different pictures or at the same time, by reusing the picture of the phototype estimation step 102 for the apparent age estimation step 101.

Figure 4:
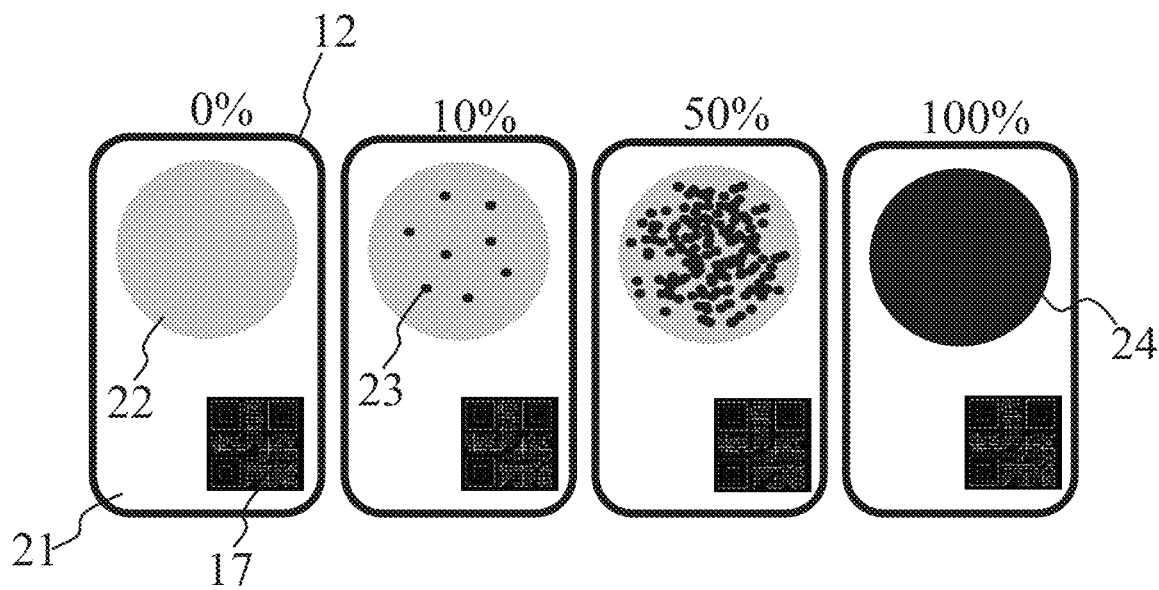
FIG. 4 is a simplified front view of four sebum patches used on users having different sebum rates.

A fourth step of estimation of a sebum rate 103 asks the user to place a sebum patch 12 on one or a plurality of areas of her/his face. As illustrated in FIG. 4, a sebum patch 12 comprises a reference surface 21 and a measurement surface 24 having a round, square, or rectangular shape, covered with an absorbing surface 22. Measurement surface 24 is of a characteristic color, for example, black, and absorbing surface 22 is opaque and has a different color, for example, grey or white.

Reference surface 21 also has a specific color, for example, white. Reference surface 21 is arranged next to measurement surface 24, for example, it may surround this measurement surface 24.

When sebum patch 12 is applied on a skin area comprising sebum, absorbing surface 22 absorbs its sebum. Thereby, the area 23 of the absorbing surface 22 having absorbed the sebum becomes transparent. It then becomes possible to at least partly see measurement surface 24 through this transparent area 23. Thus, as illustrated in FIG. 4, the more measurement surface 24 is visible, the more absorbing surface 22 has absorbed sebum on the user's skin and the more "oily" her/his skin can be considered.

To automatically calculate her/his sebum rate 103, the user must take a picture of sebum patch 12. A recognition algorithm is used to recognize the shape of measurement surface 24. Several types of algorithms may be used, such as neural networks, statistic analysis, hidden Markov models, or also graph isomorphism search.

For example, a histogram of the intensity of the grey levels of measurement surface 24 may be generated by taking as a reference white value the color of reference surface 21. An analysis of this histogram enables to determine two Gaussian envelopes corresponding to the dark areas, associated with the presence of sebum, and to light areas, associated with the absence of sebum. Thus, a segmentation of the pixels into two areas enables to calculate a sebum density per surface area unit and to estimate the user's resulting sebum rate according to a classification scale.

Figure 5:
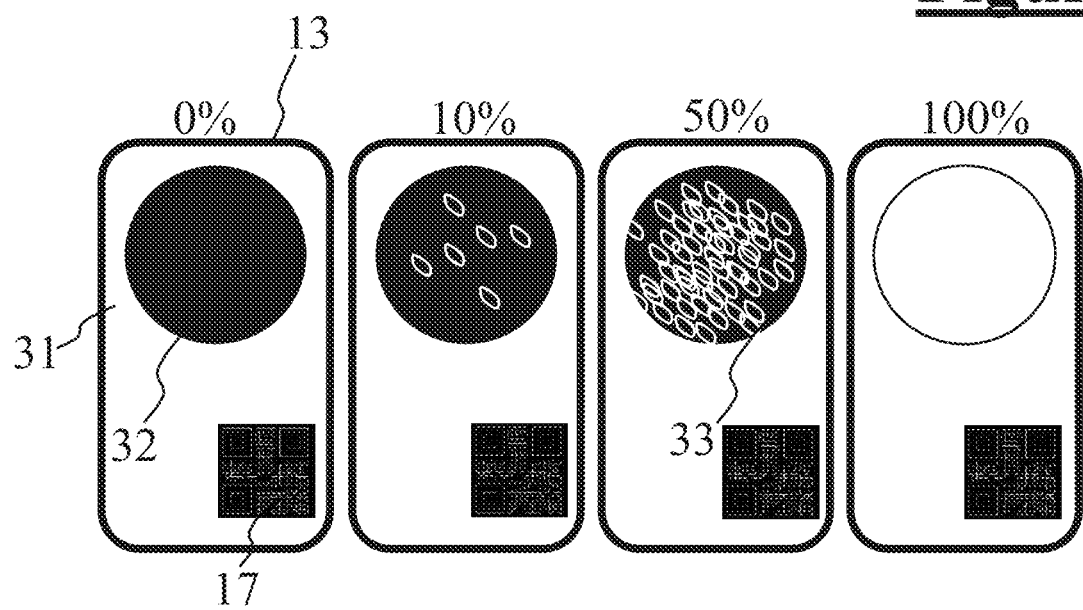
FIG. 5 is a simplified front view of the peeling patches used on users having different scale rates.

A fifth and last step of estimation of a scale rate 103 asks the user to place a peeling patch 13 on one or a plurality of areas of her/his face. As illustrated in FIG. 5, a peeling patch 13 comprises a measurement surface 32 of round, square, or rectangular shape and a reference surface 31. Measurement surface 32 has a preferably dark characteristic color, for example, black. Reference surface 31 also has a specific color, for example, white.

Reference surface 31 is arranged next to measurement surface 32, for example, it may surround this measurement surface 32.

When peeling patch 13 is applied to a skin area, measurement surface 32 tears off the surface portion of the skin, formed of dead cells 33 of light color. Thus, as illustrated in FIG. 5, the more measurement surface 32 is covered with dead cells, the more measurement surface 32 will have a light color and the more the user's skin will be considered as dehydrated.

To automatically calculate her/his scale rate 104, the user must take a picture of peeling patch 13. A recognition algorithm is used to recognize the shape of measurement surface 32. Several types of algorithms may be used, such as neural networks, statistic analysis, hidden Markov models, or also graph isomorphism search.

For example, an intensity histogram of the grey levels of measurement surface 32 may be generated by taking as a reference white value the color of reference surface 31. An analysis of this histogram enables to determine two Gaussian envelopes corresponding to light areas, associated with the presence of dead cells 33, and to dark areas, associated with the absence of dead cells 33. Thus, a segmentation of the pixels into two areas enables to calculate a scale density per surface area unit and to estimate the user's resulting scale rate according to a classification scale.

These steps may altogether be carried out in a different order without changing the invention. Similarly, the recommendations for positioning the patches on the face may vary without changing the invention.

For example, the beauty diagnosis may require placing a sebum patch 12 on the left cheekbone, a sebum patch 12 on the forehead, and a peeling patch 13 on the right cheekbone. A user having a high sebum rate at the level of the left cheekbone will be considered as having an "oily" skin.

As illustrated in FIGS. 4 and 5, the patches may also comprise an identification element 17 such as a QR code, a bar code, or any other distinctive sign enabling to identify the nature of the patch and to ensure a traceability of the batches.

As a conclusion, the invention enables to determine a beauty ritual associated with a specific user, limiting product purchase costs for the user as well as the environmental footprint and taking into account the user's lifestyle and environment to offer an anticipative ritual enabling to act before the skin's physiological parameters are modified.

What is claimed is:

1. A method of determining a skin or hair beauty ritual associated with a specific user, said method comprising the steps of:
    performing at least one beauty diagnosis of said user;
    determining a generic beauty ritual comprising a set of recommended products, said recommended products being selected according to said at least one beauty diagnosis, each recommended product being associated with a generic dosage and a generic prescription for use;
    applying a first feedback loop to the generic beauty ritual by:
        measuring, over time, the external stress undergone by said user with at least one environment sensor carried by said user during a period; and
        at each increment of said period, iteratively modifying said generic dosage and/or said generic prescription for use of said generic beauty ritual according to the external stress measured since the beginning of said period, to obtain, at each increment of said period, a refined beauty ritual with recommended products having a dosage and/or a prescription for use enabling to respond to the external stress undergone through said user's lifestyle; and
    applying a second feedback loop to the generic beauty ritual by:
        establishing, at regular intervals, at least one additional beauty diagnosis of said user, said at least one additional beauty diagnosis comprising estimating, by means of concrete physiological parameters, the variation of the skin quality of the user, and
        at each increment of said regular intervals, modifying said generic beauty ritual according to said at least one additional beauty diagnosis to obtain, at each increment of said regular intervals, a beauty ritual with recommended products having a dosage and/or a prescription for use enabling to respond to said at least one additional beauty diagnosis,
    thereby determining a skin or hair beauty ritual associated with a specific user.

2. The method of claim 1, wherein said at least one beauty diagnosis comprises a questionnaire configured to determine the needs and the beauty habits of said user.

3. The method of claim 1, further comprising estimating an age of said user's skin, wherein estimating the age comprises:
    taking a picture of said user's face;
    detecting a matrix of characteristic points on said picture; and
    determining the age of said user's skin by means of a neural network configured to analyze the position of said characteristic points and comparing these positions with the positions of characteristic points of reference faces for which the person's age is known.

4. The method of claim 1, further comprising estimating a phototype of said user, wherein estimating the phototype comprises:
    taking a picture including said user's face and a colorimetric patch comprising a reference color scale;
    comparing an average color of said user's face with the different reference colors present on said colorimetric patch; and
    determining a phototype of said user according to a maximum similarity between said average color and a color among the different reference colors present on said colorimetric patch.

5. The method of claim 4, wherein estimating the phototype uses a colorimetric patch comprising the 6 colors of Fitzpatrick's classification.

6. The method of claim 1, further comprising estimating a sebum rate of a specific area of said user's face, wherein estimating the sebum rate comprises:
    applying a sebum patch to said specific area of said user's face, wherein said sebum patch comprises a reference surface and a measurement surface covered with an absorbing surface, wherein said measurement surface and said absorbing surface comprising two distinct colors, and wherein said reference surface comprises a reference color;
    removing said sebum patch after a predetermined time period, so that said absorbing surface becomes at least partially transparent by absorbing the sebum present on said specific area of said user's face, wherein said measurement surface becomes at least partially visible;

taking a picture of said sebum patch in such a way as to include said reference surface and said measurement surface; and determining, on the picture, the sebum rate by analysis of a transparency percentage of said absorbing surface with respect to said reference color.

7. The method of claim 6, wherein estimating the sebum rate is carried out several times on a plurality of specific areas of said user's face.

8. The method of claim 1, further comprising estimating a scale rate of a specific area of said user's face, wherein estimating the scale rate comprises:

applying a peeling patch on said specific area of said user's face, wherein said patch comprises an adhesive measurement surface and a reference surface having two distinct colors;

removing said peeling patch after a predetermined time period, so that said adhesive measurement surface has a modified appearance due to the presence of dead cells;

taking a picture of said peeling patch in such a way as to include said adhesive measurement surface and said reference surface; and determining, on the picture, a scale rate by analysis of a percentage of said adhesive surface modified by the presence of dead cells with respect to a color of said reference surface.

9. The method of claim 8, wherein determining the scale rate is carried out via a neural network configured to compare the percentage of said adhesive surface modified by the presence of dead cells with reference images having a percentage of said modified adhesive surface corresponding to a determined scale rate.

10. The method of claim 6, wherein said sebum patch comprises an identification element, wherein said picture being taken by incorporating said identification element so that determining the sebum rate can be carried out by identifying the nature of the patch.

11. The method of claim 8, wherein said peeling patch comprises an identification element, wherein said picture being taken by incorporating said identification element so that determining the scale rate can be carried out by identifying the nature of the patch.

12. The method of claim 1, wherein the at least one environment sensor is integrated in a connected jewel or watch.

13. A method of determining a skin or hair beauty ritual associated with a specific user, said method comprising the steps of:

performing a first beauty diagnosis of said user;

determining a generic beauty ritual comprising a set of recommended products, said recommended products being selected according to said first beauty diagnosis, each recommended product being associated with a generic dosage and a generic prescription for use;

measuring, over time, the external stress undergone by said user with at least one environment sensor carried by said user during a period;

recursively varying a dosage and/or a prescription for use of said generic beauty ritual at each increment of said period, according to the external stress measured since the beginning of said period, to obtain, at each increment of said period, a refined beauty ritual with recommended products having a dosage and/or a prescription for use enabling to respond to the external stress undergone through said user's lifestyle; and establishing, at the end of at least one regular interval, at least one additional beauty diagnosis of said user, wherein each of the at least one additional beauty diagnoses comprises a plurality of steps of analysis of physiological and psychological parameters of said user, and, iteratively modifying said refined beauty ritual at each increment of said regular intervals, according to the additional beauty diagnosis to obtain, at each increment of said regular intervals, a beauty ritual with recommended products having a dosage and/or a prescription for use enabling to respond to the additional beauty diagnosis.

14. A method of determining a skin or hair beauty ritual associated with a specific user, said method comprising the steps of:

performing a first beauty diagnosis of said user;

determining a generic beauty ritual comprising a set of recommended products, said recommended products being selected according to said first beauty diagnosis, each recommended product being associated with a generic dosage and a generic prescription for use; and refining the generic beauty ritual over time based on at least two iterative steps repeated at regular intervals;

wherein a first iterative step comprises:

measuring, over time, the external stress undergone by said user with at least one environment sensor carried by said user during a period; and at each increment of said period, iteratively modifying said generic dosage and/or said generic prescription for use of said generic beauty ritual according to the external stress measured since the beginning of said period, to obtain, at each increment of said period, a refined beauty ritual with recommended products having a dosage and/or a prescription for use enabling to respond to the external stress undergone through said user's lifestyle; and wherein a second iterative step comprises:

establishing, at least one additional beauty diagnosis of said user, said at least one additional beauty diagnosis comprising estimating, by means of concrete physiological parameters, the variation of the skin quality of the user, and modifying said generic beauty ritual according to said at least one additional beauty diagnosis to obtain a beauty ritual with recommended products having a dosage and/or a prescription for use enabling to respond to said at least one additional beauty diagnosis, thereby determining a skin or hair beauty ritual associated with a specific user.

* * * * *